United States Patent [19]

Sawai et al.

[11] Patent Number: 5,180,739
[45] Date of Patent: Jan. 19, 1993

[54] USE OF 3-OXYGERMYLPROPIONIC ACID TO TREAT AND PREVENT DIABETES-DEPENDENT TYPE OF AUTOIMMUNE DISEASES

[75] Inventors: Kiichi Sawai; Masayasu Kurono; Takahiko Mitani; Masanori Nagabuchi; Keizo Anzai, all of Nagoya, Japan

[73] Assignee: Sanwa Kagaku Kenkyusho Co., Ltd., Nagoya, Japan

[21] Appl. No.: 659,649

[22] Filed: Feb. 23, 1991

[30] Foreign Application Priority Data

Feb. 28, 1990 [JP] Japan .................................. 2-48644

[51] Int. Cl.$^5$ ............................................. A61K 31/27
[52] U.S. Cl. ....................................................... 514/491
[58] Field of Search ........................................... 514/491

[56] References Cited

U.S. PATENT DOCUMENTS 4,889,715 12/1989 Sawai .................................... 424/80

FOREIGN PATENT DOCUMENTS 61-151123 12/1984 Japan .
60-190714  9/1985 Japan .
61-65819  4/1986 Japan .

Primary Examiner—S. J. Friedman
Attorney, Agent, or Firm—Armstrong & Kubovcik

[57] ABSTRACT

A pharmaceutical composition is used to treat and prevent a diabetes-dependent type of autoimmune diseases, said pharmaceutical composition comprising a therapeutically effective amount of 3-oxygermylpropionic acid represented by the following formula:

$$[(O_{\frac{1}{2}})_3 GeCH_2CH_2CO_2H]_n$$

wherein n stands for an integer of 1 or more, optionally with an activating carrier.

4 Claims, 3 Drawing Sheets

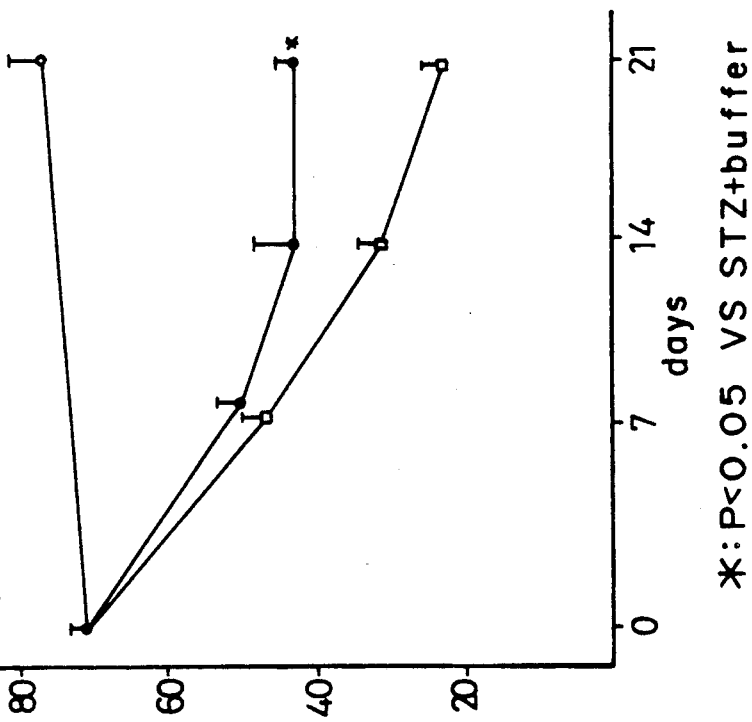

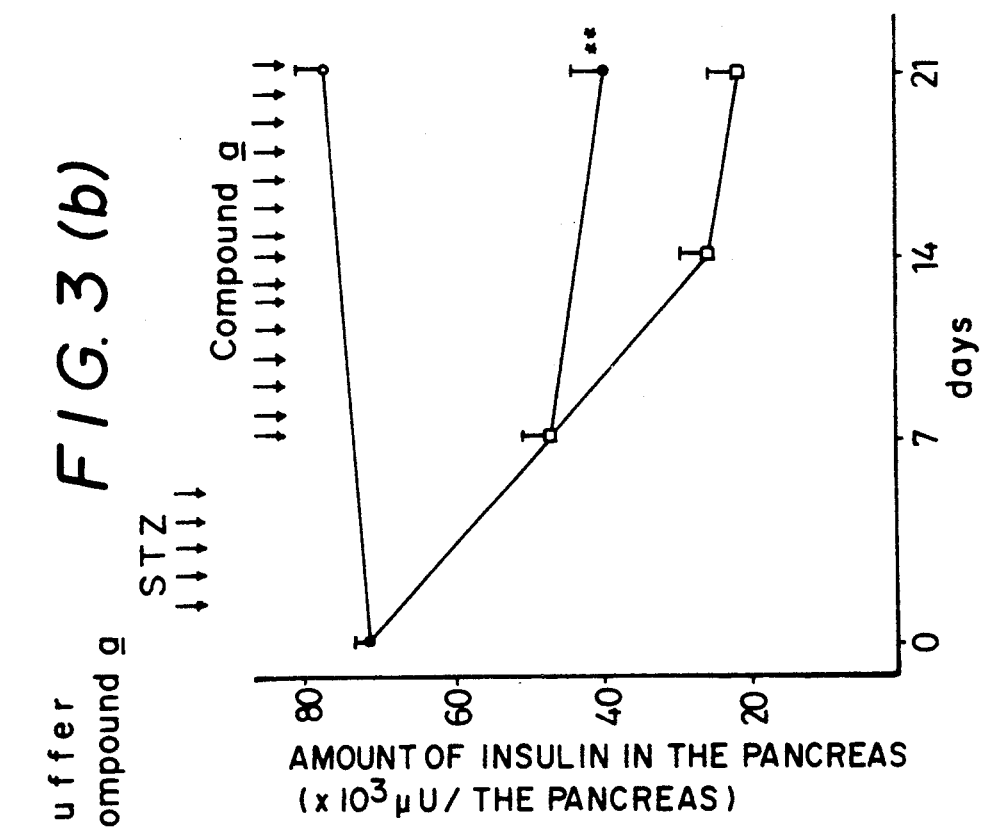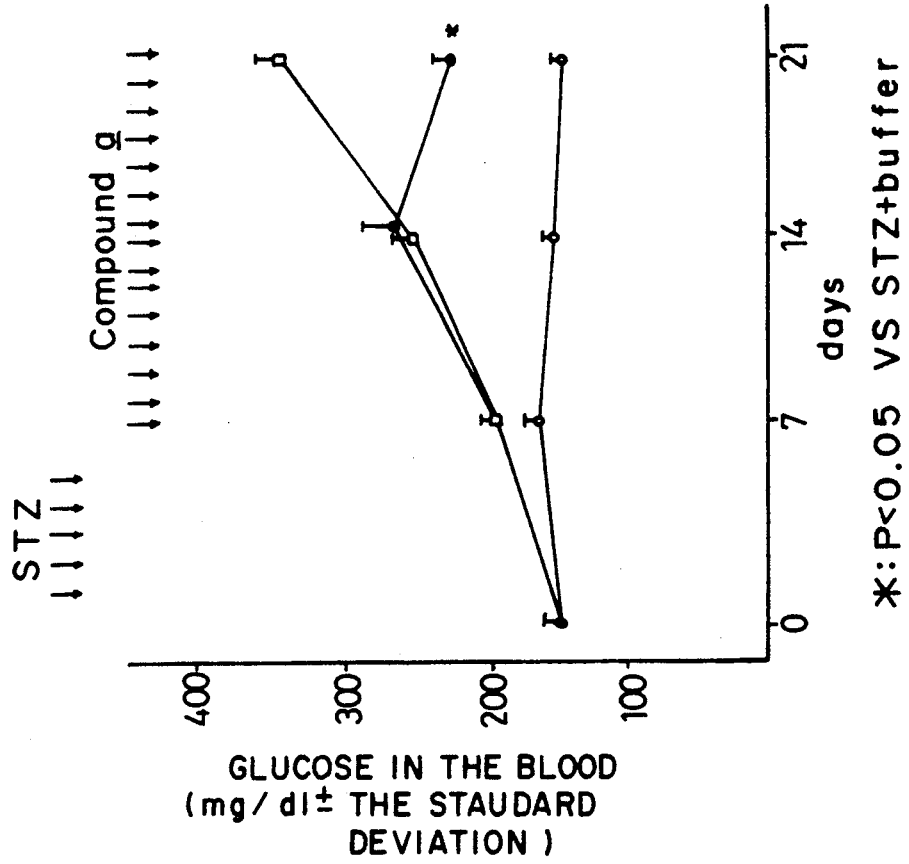

USE OF 3-OXYGERMYLPROPIONIC ACID TO TREAT AND PREVENT DIABETES-DEPENDENT TYPE OF AUTOIMMUNE DISEASES

BACKGROUND OF THE INVENTION

1. Field of the Invention

The present invention relates to a pharmaceutical composition for treating and preventing diabetes-dependent type of autoimmune diseases, which contains as an active ingredient a compound represented by the following formula:

$$[(O_\frac{1}{2})_3GeCH_2CH_2CO_2H]_n \qquad (I)$$

wherein n stands for an integer of 1 or more, optionally in combination with an activation carrier.

The compound used in this invention is in the form of a white acicular crystal having such physicochemical properties as expressed in terms of a specific gravity or density of 2.23, a solubility in water of 1.57 at 20 and a melting or decomposition point of about 230.

2. Prior Art

Having sophisticated polymerizability and a variety of applications, the compound represented by Formula I or 3-oxygermylpropionic acid has recently attracted public attention in view of its pharmacological activity. This compound, according to some suggestion, has the potentiality of being usable as therapeutic drugs for hepatophathy. However, a serious problem with 3-oxygermylpropionic acid is that it is so unstable in the presence of water that its pharmacological activity decreases drastically (see Japanese Patent Publication No. Sho 57-53800 and U.S. Pat. No. 4,309,412).

As a result of having made strenuous investigations to maintain the inherent pharmacological activity of 3-oxygermylpropionic acid in a stable manner, the inventors have already found out that a variety of specific substances can be effectively used as stabilizers therefor (see Japanese Patent Kokai Publication No. Sho 61-65819) and saccharides can enhance the activity thereof (see Japanese Patent Kokai Publication No. Sho 60-190714). The inventors have also discovered that 3-oxygermylpropionic acid has immunity-accommodative actions (see Japanese Patent Kokai Publication No. Sho 61-161123).

Patients with deblitated blood sugar-accommotative functions, esp. those with diabetes are likely to have toxic symptoms due to their antidotal hypometabolism or immunodeficiency and so suffer disorder such as allergy, anaphylaxis, cataract, cutaneous ulcers and acute insufficiency or, reportedly, die in the worst case. Such disorders by and large are considered due to autoimmune diseases.

SUMMARY OF THE INVENTION

Study after study has turned out that 3-oxygermylpropionic acid, which is of great safety and has such physicochemical properties as expressed in terms of a specific gravity or density of 2.23, a solubility in water of 1.57 at 20 and a melting or decomposition point of about 230, is efficacious against a diabetes-dependent type of autoimmune diseases.

More specifically, the present invention provides a pharmaceutical composition greatly efficacious against various diabetic diseases, esp. autoimmune diseases, which contains as an active ingredient 3-oxygermylpropionic acid represented by Formula I:

$$[(O_{1/2})_3GeCH_2CH_2CO_2H]_n \qquad (I)$$

wherein n stands for an integer of 1 or more, optionally in combination with an activating carrier. Preferably, the activating carrier is hydroxypropylcellulose, which is used in an amount of 0.005 to 50% by weight per 0.005 to 5% by weight of the active ingredient.

BRIEF DESCRIPTION OF THE DRAWINGS

FIGS. 2(a) and 2(b) are graphs showing the concentration of glucose in the blood and the amount of insulin in the pancreas measured with a mouse in accordance with Test Example 2, and FIGS. 3(a) and 3(b) are graphs showing the concentration of glucose in the blood and the amount of insulin in the pancreas measured with a mouse in accordance with Test Example 3.

DETAILED DESCRIPTION OF THE INVENTION

Figure 1B:
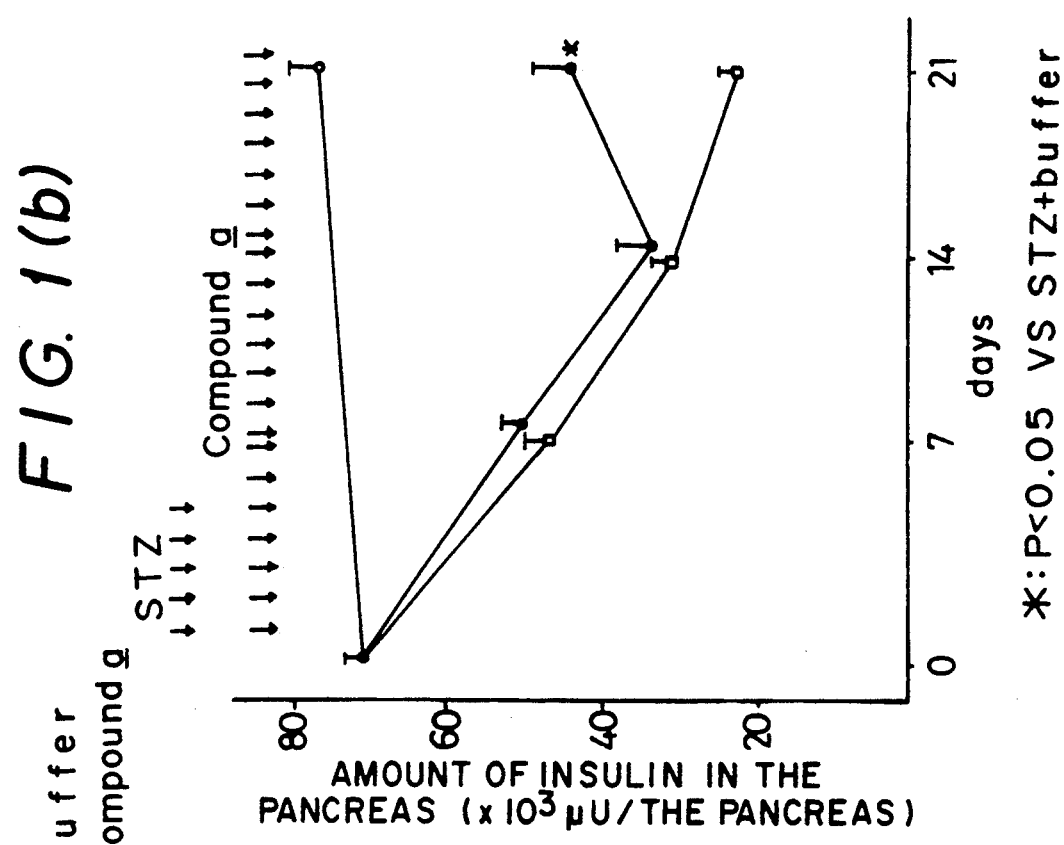
FIGS. 1(a) and 1(b) are graphs showing the concentration of glucose in the blood and the amount of insulin in the pancreas measured with a mouse in accordance with Test Example 1.

As so far described, 3-oxygermylpropionic acid is of polymerizability so sophisticated that it can become very unstable in the presence of moisture, thus resulting in a sharp drop of its pharmacological activity. For that reason, it is desired to add a preparatory carrier or a pharmacologically activating carrier to the composition according to this invention and thereby stabilize it.

Composition containing 3-oxygermylpropionic acid alone, for instance, are usually provided in the form of orally administered tablets or capsules which are absorbed through digestive tracts.

It is noted that although varying dependent upon the type of compound, the type of composition, the age of patient, etc., the composition according to this invention may generally be administered to humans at a dose between 10 mg/kg and 1500 mg/kg. A preferable daily dose to adult patients (weighing 50 kg) is about 150 mg.

EXAMPLES

The present invention will now be explained more illustratively but not exclusively with reference to the following examples.

PREPARATIVE EXAMPLE 1

Preparation of the Primary Composition

Hydroxypropylcellulose and 3-oxygermylpropionic acid represented by Formula I were mixed together at 2:1. The mixture was kneaded with ethanol serving as a wetting agent and then dried at a temperature lower than 50° C. to obtain a powdery or granular composition.

PREPARATIVE EXAMPLE 2

Tablet

The primary composition was blended with an vehicle, etc. according to the following formulation, and tableted in conventional manners to obtain tablets.

| Ingredients | Amount (mg) |
|---|---|
| Primary composition | 100 |
| Lactose | suitable |
| Carboxymethylcellulose (Ca) | 7 |
| Crystalline cellulose | 40 |
| Magnesium stearate | 7 |
| | 200 mg per tablet |

PREPARATION EXAMPLE 3

Capsule

The primary composition was blended with a vehicle according to the following formulation, and encapsulated in conventional manners.

| Ingredients | Amount (mg) |
|---|---|
| Primary composition | 100 |
| Lactose | 40 |
| Corn starch | 38 |
| Magnesium stearate | 2 |

Toxicity Tests

Acute and subacute (chronic) toxicity tests were performed using SD rats and mice which has received 3-oxygermylpropionic acid represented by Formula I (hereinafter referred to Compound a) and the above-mentioned primary composition (hereinafter called Composition b). The results are reported below.

For experimentation, a group of 8-10 animals were used.

(1) Acute Test

| LD 50 (mg/kg) | Oral administration (no significant difference between Compound a and Composition b |
|---|---|
| Mice, | |
| male | 5,600 or more |
| female | 5,800 or more |
| Rats. | |
| male | 7,700 or more |
| female | 7,050 or more |

Between Compound a and Composition b there was no significant difference in acute toxicity, but the group which received Compound a alone showed general symptoms of appeasement, diarrhea, vomiting and typhlectasis. The group which received Composition b, on the other hand, did not substantially have any particular symptom.

(2) Subacute Test

Over 3 months, Compound a and Composition b were orally administered to two groups of SD male rats at doses of 256, 380, 640, 1300, 1600 and 4000 mg/kg/day to determined which dose to have no toxic influence at all and which dose to induce positive poisoning.

Compound a had no toxic influence whatsoever at 256 mg/kg but induced positive poisoning at 1600 mg/kg. Some animals were sacrificed at 4000 mg/kg. Toxic symptoms then disappeared by no drug treatments over 5 weeks.

Composition b had no toxic influence whatsoever at 380 mg/kg but induced positive poisoning at 1300 mg/kg. No animals were sacrificed.

Pharmaceutical Tests

Continuous 5-day administration of streptozocin (STZ) to an AKR/J1 line mice, that ia an inbred mice with a spontaneous symptom of leukemia, can cause it to take a disease similar to human Type I diabetes (dependent upon insulin). Tests were performed for the purpose of going into influence Compound a and Composition b have on such a mice with streptozosin-induced diabetes.

TEST EXAMPLE 1

(a) Procedures

Streptozocin (STZ) was continuously administrated to the abdominal cavity of a (masculine) mouse belonging to AKR/J1 at a dose of 40 mg/kg for 5 days to induce an increase in the concentration of glucose in the blood and a decrease in the amount of insulin in the pancreas.

With Compound a dissolved in a phosphate buffer solution with pH 7.4, the concentration of glucose in the blood was measured at 7 days, 14 days and 21 days from STZ dosing, using a GOD-PAP kit (made by Boehringer Mannheim) based on the glucose oxidase process for measurement. In addition, the amount of insulin in the pancreas, extracted by the acid-ethanol process, was assayed with a radio immuno assay kit (made by Pharmacia Aktiebolag) based on an immunoassay process making use of a competitive reaction by $^{125}$I-labeled insulin (see Soeldner, JS & Slone, D, "Diabetes", Vol. 14, pp. 771-779, 1985).

(b) Results

Figure 1A:
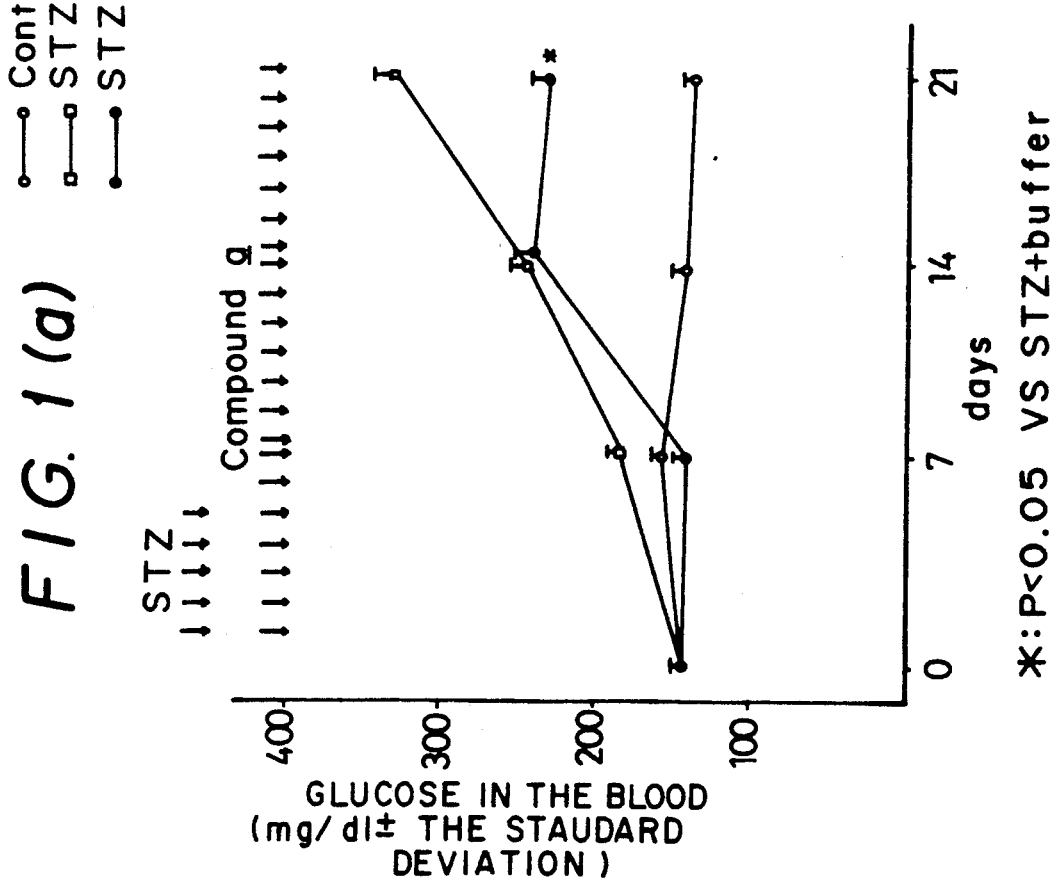

The concentration of glucose in the blood and the amount of insulin in the pancreas, as measured, are shown in the graphs depicted in FIGS. 1(a) and 1(b). The graphs indicate that at 21 days from dosing, Compound a could give rise to significant improvements in the concentration of glucose in the blood increased and the amount of insulin in the pancreas decreased by the administration of STZ at a rejection rate of 5%.

TEST EXAMPLE 2

(a) Procedures

A similar mouse was caused to develop STZ-induced diabetes in a similar manner as referred to in Test Example 1.

A solution of Compound a in a phosphate buffer with pH 7.4 was continuously administered to the abdominal cavity of the animal at 5 mg/kg over 7 days from STZ dosing.

At 7 days, 14 days and 21 days from STZ dosing, the concentration of glucose in the blood and the amount of insulin in the pancreas were measured in similar manners as mentioned in Test Example 1.

(b) Results

The concentration of glucose in the blood and the amount of insulin in the pancreas, as measured, are shown in the graphs depicted in FIGS. 2(a) and 2(b). The graphs indicate that at 21 days from dosing, Compound a could give rise to significant improvements in the concentration of glucose in the blood increased and the amount of insulin in the pancreas decreased by the administration of STZ at a rejection rate of 5%.

TEST EXAMPLE 3

(a) Procedures

A similar mouse was caused to develop STZ-induced diabetes in a similar manner as referred to in Test Example 1.

A solution of Compound a in a phosphate buffer with pH 7.4 was continuously administered to the abdominal cavity of the animal at 5 mg/kg 15 days from the 7th day after STZ dosing.

At 7 days, 14 days and 21 days from STZ dosing, the concentration of glucose in the blood and the amount of insulin in the pancreas were measured in similar manners as mentioned in Test Example 1.

(b) Results

The concentration of glucose in the blood and the amount of insulin in the pancreas, as measured, are shown in the graphs depicted in FIGS. 3(a) and 2(b). The graphs indicate that at 21 days from dosing, Compound a could give rise to significant improvements in the concentration of glucolse in the blood increased and the amount of insulin in the pancreas decreased by the administration of STZ at a rejection rate of 5%.

TEST EXAMPLE 4

(a) Procedures

Similar mice were caused to develop STZ-induced diabetes in a similar manner as described in Test Example 1.

A solution of Compound a in a similar phosphate buffer with pH 7.4 as used in Test Example 1 was continuously administrated at a rejection rate of 5% to the abdominal cavities according to similar dosing schemes as applied in Test Examples 1, 2 and 3.

At 21 days from STZ dosing, the degree of cellular infiltration in the Langerhans' islands were assayed under an optical microscope.

(b) Results

The degree of cellular infiltration in the Langerhans' islands, as assayed, are reported in Table 1. The results indicate that at 21 days from its dosing, Compound a successfully decreased the infiltrated cells increased by STZ dosing, ameliorating the conditions.

TABLE 1

| Degrees of cellular infiltration in the Langerhans' islands of mice | | | | | |
|---|---|---|---|---|---|
| | Degrees of pancreatitis, % | | | | Incidence of pancreatitis (%) (I-III) |
| | 0 (0%) | I (0-25%) | II (25-50%) | III (50-100%) | |
| STZ + Buffer | 32 | 40 | 11 | 17 | 68 |
| STZ + a (1-21 days) | 70 | 25 | 4 | 1 | 30 |
| STZ + a (1-7 days) | 70 | 23 | 4 | 3 | 30 |
| STZ + a (1-21 days) | 68 | 30 | 1 | 1 | 32 |

From the results of the pharmaceutical tests, it can be understood that the compositions according to this invention are greatly efficacious against STZ-induced diabetes similar to the human diabetes model. Thus, they can be used as an active ingredient for diabetes-treating drugs.

What is claimed is:

1. A method of treating diabetes in mammals requiring such treatment, comprising administering to said mammal a therapeutically effective amount of 3-oxygermylpropionic acid represented by the formula $$[(O_{1/8})_3GeCH_2CO_2H]_n$$

wherein n stands for an integer of 1 or more.

2. A method according to claim 1, further comprising an activating carrier.

3. A method according to claim 2, wherein said activating carrier is hydroxypropylcellulose.

4. A method according to claim 3, wherein said hydroxypropylcellulose is present in an amount of 0.005 to 50% by weight per 0.005 to 5% by weight of said 3-oxygermylpropionic acid.

* * * * *

UNITED STATES PATENT AND TRADEMARK OFFICE
CERTIFICATE OF CORRECTION

PATENT NO. : 5,180,739
DATED : January 19, 1993
INVENTOR(S) : Kiichi Sawai, et al It is certified that error appears in the above-indentified patent and that said Letters Patent is hereby corrected as shown below:

On title page, item [75] add the following inventor:

--Shoji Yokochi--

Signed and Sealed this

Twenty-second Day of March, 1994

Attest:

BRUCE LEHMAN

Attesting Officer      Commissioner of Patents and Trademarks